(12) United States Patent
Chen et al.

(10) Patent No.: US 6,168,701 B1
(45) Date of Patent: Jan. 2, 2001

(54) METHODS AND COMPOSITIONS FOR IMPROVING THE LOADING OF ANALYTICAL INSTRUMENTS

(75) Inventors: Shiaw-Min Chen, San Jose; Cheryl R. Heiner, La Honda; Adam L. Lowe, San Francisco, all of CA (US)

(73) Assignee: The Perkins-Elmer Corporation, Foster City, CA (US)

( * ) Notice: Under 35 U.S.C. 154(b), the term of this patent shall be extended for 0 days.

(21) Appl. No.: 09/303,789

(22) Filed: Apr. 30, 1999

(51) Int. Cl.[7] .................. G01N 27/26; G01N 27/447

(52) U.S. Cl. .................. 204/456; 204/466; 204/467; 204/606; 436/172; 436/174; 422/61

(58) Field of Search .................. 204/456, 457, 204/465, 466, 467, 468, 606, 616, 617, 618; 436/172, 174; 422/61

(56) References Cited

FOREIGN PATENT DOCUMENTS

WO 00/40959 * 7/2000 (WO).

* cited by examiner

*Primary Examiner*—Jill Warden
*Assistant Examiner*—John S Starsiak. Jr.
(74) *Attorney, Agent, or Firm*—Scott R. Bortner

(57) ABSTRACT

The invention relates to improved methods and compositions for loading samples into an analytical instrument having a plurality of sample receiving loading ports. In a principle embodiment of the invention, first and second sample markers are added to sample to be loaded onto an analytical instrument having a plurality of sample receiving loading ports. The first and second samples are compounds are selected so as to produce a distinctive signal upon combination thus a sample containing a first sample marker and a sample containing a second marker are mistakenly loaded into the same sample receiving loading port, a detectable signal indicative of the misloading is produced.

16 Claims, No Drawings

METHODS AND COMPOSITIONS FOR IMPROVING THE LOADING OF ANALYTICAL INSTRUMENTS

BACKGROUND

The loading of samples into analytical instruments presents numerous opportunities for making errors. This problem is particularly acute in apparatus designed to simultaneously receive and analyze multiple samples. There is a significant chance of loading samples into the wrong loading port of an apparatus having multiple loading ports, thus resulting in the unwanted mixing of samples or the misidentification of samples. It is of particular interest to reduce the loading error associated with electrophoresis apparatus. Many electrophoresis devices have multiple loading ports for introducing sample into an instrument, e.g., loading wells, that are in close proximity to one another and also similar in appearance. Loading errors are common problems in manually loaded electrophoresis apparatus and similar devices. Thus, it is of interest to provide methods for reducing loading errors in analytical instruments, particularly electrophoresis devices.

In order to solve the aforementioned loading problems, the inventors have provided improved methods and compositions for loading analytical apparatus in which signals are produced upon misleading. Furthermore, the invention may be readily adapted to use in many different types of apparatus. The invention also includes methods of identifying regions, e.g., lanes or channels, of electrophoresis apparatus (or similar apparatus) that may be combined with the subject methods and reagents for improving the loading of apparatus.

SUMMARY

The invention relates to improved methods and compositions for loading samples into an analytical instrument having a plurality of sample receiving loading ports. In a principle embodiment of the invention, first and second sample markers are added to sample to be loaded onto an analytical instrument having a plurality of sample receiving loading ports. The first and second samples are compounds are selected so as to produce a distinctive signal upon combination. Thus a sample containing a first sample marker and a sample containing a second marker that are mistakenly loaded into the same sample receiving loading port would produce a detectable signal indicative of the misleading.

One embodiment of the invention is a method of loading an analytical instrument having a plurality of sample receiving ports. A slab gel electrophoresis apparatus for DNA fragment length analysis is an example of such a device. A first sample comprising a first substance for analysis and a first sample marker is loaded onto a first sample loading port. A second sample comprising a second substance for analysis and a second sample marker is added to a second sample loading port. As previously noted, the first and second samples markers produce a detectable signal if they contact one another. Thus the apparatus may be inspected for the presence of the detectable signal.

Other embodiments of the subject invention are reagent sets for use in loading analytical instruments having plurality of sample loading ports. The reagents in the subject reagent sets are for addition to samples for loading into the loading ports of an analytical instrument having a plurality of loading ports. The subject reagent sets include a first sample addition reagent and a second sample addition reagent. The first reagent comprises a first sample marker and a first channel indicator. The second sample addition reagent sets also includes a second sample marker and a second channel indicator. The first and second sample markers are selected so as to produce a detectable signal if they contact one another. The first and second channel indicators are indicator markers that serve to distinguish one channel from another. The first and second channel indicators may be distinguishable from one another. In embodiments of the subject reagent sets for use with analytical instruments that are electrophoresis separation devices, the first and second channel indicators migrate in the separatory electric field of the instrument. In embodiments of the subject reagent for use with fluorescence detection electrophoresis systems.

DESCRIPTION OF SPECIFIC EMBODIMENTS

The invention relates to methods and compositions for improving the loading of analytical instruments having a plurality of sample loading ports. Such analytical instruments are designed to receive different sample preparations in each port and provide for the essentially simultaneous analysis of all the samples. The subject invention may be applied to a wide variety of analytical instruments. Of particular interest is the use of the subject methods and compositions with electrophoretic apparatus using various separation matrices. Suitable electrophoretic apparatus includes, but is not limited to slab gel apparatus, capillary apparatus, paper electrophoresis apparatus, and the like. The loading wells in a electrophoresis slab gel system serve as loading ports. It is of particular interest to provide embodiments of the subject invention for use with automated florescent electrophoresis systems, e.g., the Applied Biosystems 377 (PE Biosystems, Foster City, Calif.).

The invention involves the use of a first and second sample markers that when mixed produce a detectable signal that may be distinguished from both the first and second sample markers. In one embodiment of the invention, a sample containing a substance for analysis and a first sample marker is introduced into a first loading port on the apparatus. A second sample containing a substance for analysis and a second sample marker is introduced into a second loading port on the same apparatus. The apparatus is subsequently observed for the presence of the detectable signal indicative of the mixing of the first and second sample markers, and thus identifying a loading error. It will be appreciated that such a method can be readily applied to any similar apparatus regardless of the actual number of loading ports (provided there are at least two loading ports). For example, fifty samples may be divided into two groups of twenty-five samples each, wherein one group comprise the first sample marker and the second group containing the second sample marker. Samples containing the different sample markers may be loaded to alternate loading ports so as to maximize the changes of discovering a loading error.

A wide variety of compounds may be used as sample markers. As the first and second sample markers are selected so as to produce a detectable signal upon contact with one another, the choice of the first sample marker will limit the range of potential second markers. Examples of classes compounds that may be used as sample markers include small organic molecules (such as dyes), proteins, carbohydrates, and inorganic molecules. Preferably, the sample markers are soluble or partially soluble in the solution that comprises samples for analysis. Other examples of first and second sample marker combinations include enzyme and substrates recognized by the enzyme, particularly colorimetric or chemiluminescent substrates. Typically, although not necessarily, sample solutions for use with sample markers are aqueous solutions. The sample markers are selected so as to not to interact with the components of the sample for analysis in such a way as to interfere with the detection of manipulation of the sample of interest by the given analytical instrument.

The first and second sample markers are selected so as to produce a detectable signal upon contacting one another. The detectable signal is selected so as to be discernable in the presence of either the first or the second sample marker. The detectable signal may take on any of a variety of manifestations. The production of a detectable signal may or may not involve a chemical reaction. In one embodiment of the invention, the first and second sample markers are selected so as to chemically react with one another to produce a detectable reaction product. Examples of such manifestations include, but are not limited to, colormetric signal, chemiluminescent signals, precipitate formation, formation of a gaseous phase, change in heat content, and the like. Preferably, the detectable signal formed is a signal capable of being recognized by unaided human perception, e.g., the naked eye, thus avoiding the need for additional instrumentation. Alternatively, the detectable may be undetectable to unaided human perception. It is also of interest to generate detectable signals that may be detected by a machine sensory system, thereby enabling the partial or complete automation of an instrumentation system.

In a preferred embodiment of the inventions, the first and second sample markers are two dyes that are resolvable by the human eye using visible light. The dyes do not need to chemically interact with one another. For example a first sample marker may be Blue Dextran (blue under visible light) and the second sample marker may be Disperse Red (red under visible light). Upon mixing a detectable signal that is purple in color is produced. A person skilled in the art may easily produce other color combinations using commercially available colored compounds.

In one embodiment of the invention, a plurality of samples for loading into an analytical instrument are prepared. Sample markers are subsequently added to some, and more preferably all, of the samples for loading. Different sample markers are added to different samples. A different sample marker may be added to each sample such that the number of different sample markers for a given loading is equivalent to the number of samples. Alternatively, the number of different sample markers may be less than the total number of samples used for a given loading. In a preferred embodiment of the invention, the samples for loading onto an apparatus are arranged in the same order (typically linear ordering) as the order in which the samples are to be loaded onto the apparatus. The sample may be placed in order for loading and the different sample markers added to the arranged samples. In a preferred embodiment of the invention, two different sample markers are employed, irrespective of the total number of samples used for given loading. In those embodiments of the invention employing two different markers, the samples containing the different markers are loaded into alternating sample loading ports. Disturbances in the alternating pattern may be detected when this alternating pattern is disrupted so as to produce the mixing of the first and second sample markers in a single loading port, thereby indicating a loading error.

The subject methods may be used in conjunction with a wide variety of different sample materials. Suitable sample material for analysis are dictated by the nature of the analytical instrument for use in the method. Depending upon the choice of instrument, both organic and inorganic molecules may be used. Of particular interest is the use of biological macromolecules such as nucleic acids, proteins, and carbohydrates. Of particular interest is the analysis of nucleic acids by electrophoresis. The nucleic acids for analysis include DNA fragments produced by nucleic acid amplification (e.g., PCR) and DNA fragments produced in nucleic acid sequencing reactions (e.g., Sanger-type sequencing). DNA fragments for analysis may be fluorescently labeled, thereby permitting the DNA fragments to be analyzed fluorescence detection electrophoresis apparatus (e.g., a DNA sequencer such as the Applied Biosystems 377).

The methods and reagents of the invention may also employ channel indicators. Channel indicators are molecules that serve to identify a specific channel or channels of an analytical instrument. In a preferred embodiment, a distinctive channel indicator is used for each channel in the apparatus of interest. Channel indicators are labeled (or considered to be the label itself) in such a way as to be detectable in the presence of the compounds for analysis in the samples of interest. Preferably, channel indicators are detectable (and distinguishable) by the same detection used to detect the sample compounds for analysis. The detectable signal produced from the channel indicators may take on a variety of forms. Such labels may, for example be fluorescent, chemiluminescent, radioactive, spin-labeled, colormetric and the like. In a preferred embodiment of the invention, the labels are fluorescent. Channel indicators may employ distinctive combinations of individual detectably labeled compounds or detectable labels. For example compound A may be a first channel indicator, compound B may be a second channel indicator, and the combination of compounds A and B may be used to indicate a third channel.

Channel indicators are of particular use in multi-lane electrophoresis apparatus, e.g., a slab gel. Channel indicators for use in electrophoresis apparatus are selected to be compounds that migrate in a electrical field (i.e., charged compounds) with migration properties similar to that of the compounds for analysis in the subject samples. Preferably, the labeled compounds are of the same or similar general class of compound as the compounds for analysis. For example, in an embodiment of the invention for use with fluorescently labeled DNA fragments or other nucleic acids (or analogy thereof), e.g., a sort of polynucleotide sequencing reaction products, channel indicators may be DNA fragments or other nucleic acids (or analogy thereof), that are labeled with fluorescent dyes that are spectrally distinct from the fluorescent dyes on the polynucleotides for analysis. The size of the labeled DNA fragments may also be used to provide distinctive channel indicators. For example a first channel indicator may be a 100 bp DNA fragment labeled with fluorescent dye A, a second channel indicator may be a 150 bp DNA fragment also labeled with fluorescent dye A, and a third channel indicator may be the combination of the 100 bp and 150 bp fragments each labeled with dye A. As the migration rate of DNA in electrophoresis is a function (in part) of the length of the DNA, it will be appreciated by person of skill in the art that similar differences in migration can be achieved by staggered loading of the channel indicators that are essentially structurally identical. Additional channel indicators may also take the form of additional fluorescent dyes that are spectrally distinct from the compounds for analysis.

The methods of the invention for loading of analytical instruments may also include the step of adding channel indicators to samples for loading. This addition preferably takes place prior to the loading of the samples on the instrument. For example, a first sample loaded onto an apparatus may contain (in addition to the compound for analysis) a first sample marker and a first channel indicator, and a second sample containing a second sample marker and a second channel indicator loaded onto a second loading port of the same instrument. The channel indicator and the sample markers may be added to the sample in the form of a single solution comprising both compounds, i.e., a sample addition reagent.

The channel indicators may also be added to channels (via loading ports) either before or after sample or sample markers have been introduced into the apparatus.

Another embodiment of the invention is a method for distinguishing between channels of apparatus having a plurality of sample loading ports. The method is particularly useful for use with electrophoresis apparatus, and especially so for fluorescence detection slab gel systems such as automated DNA sequencers, e.g., the Applied Biosystems 377 (PE Biosystems, Foster City Calif.). The subject methods of distinguishing between channels includes the steps of the subject methods of loading with channel indicators. The method includes the additional step of identifying the specific channel indicator in a given channel or channels. Because the specific properties of each channel indicator added to each sample is known and under the control of the user, a correlation exists that may be used to verify the identity of sample independent of it's channel location. This correlation permits confirmation of the proper loading of samples into channels (and also the loading ports). This correlating process may be automated or may be performed separately by an operator of the apparatus.

Other embodiments of the invention include reagent sets for use in the subject methods. The reagent sets of the invention include at least two sample addition reagents. The first sample addition reagent includes a first marker and a first channel indicator. The second sample addition reagent includes a second marker and a second channel indicator. The first and second sample markers in the reagent sets are the first and second markers for use in the subject method. The first and second sample markers produce a detectable signal upon combination with one another. The first and second channel indicators in the subject reagent sets are selected so as not to interfere with the detection of the detectable signal produced by the combination of the sample markers. Embodiments of the invention also include reagents having more than two different sample addition reagents. In one embodiment of the invention sample addition reagent sets may contain more distinct channel indicators than sample markers. For example a set of sample addition reagents for use with a 96 lane electrophoresis apparatus may comprise 96 separate addition reagents, wherein each sample addition reagent comprises a distinctive channel marker. Such a kit may be designed so as to have two more different markers. The sample addition reagents of such a kit may be used by setting up a correspondence between the 96 different addition reagents and 96 samples. This relationship between each specific addition reagent and each specific sample may be recorded and subsequently referred to in order to confirm proper loading of the apparatus. The sample addition reagents are preferably used such that first and second markers are added to samples to be loaded into adjacent ports, thereby providing for the detection a first and second sample marker loaded into the same loading port.

EQUIVALENTS

All publications and patent applications mentioned in this specification are indicative of the skill of those skilled in the art to which this invention pertains. All publications and patent applications are herein incorporated by reference to the same extent as if each individual publication or patent application was specifically and individually indicated to be incorporated by reference.

The foregoing written specification is considered to be sufficient to enable one skilled in the art to practice the invention. Indeed, various modifications of the above-described modes for carrying out the invention that are obvious to those skilled in the field of molecular biology or related fields are intended to be within the scope of the following claims.

What is claimed is:

1. A method of loading an analytical instrument having a plurality of sample loading ports, said method comprising,
   introducing a first sample to a first loading port, wherein the first sample comprises a first substance for analysis by the analytical instrument and a first sample marker,
   introducing a second sample to a second loading port, wherein the second sample comprises a second substance for analysis by the analytical instrument and a second sample marker, wherein a detectable signal is produced if the first sample marker contacts the second sample marker.

2. The method according to claim 1, wherein the analytical instrument is an electrophoresis apparatus.

3. The method according to claim 2, wherein the electrophoresis apparatus comprises a fluorescence detection system.

4. The method of claim 1, wherein the first and the second substances for analysis are DNA fragments.

5. The method according to claim 4, wherein the DNA fragments are produced by polynucleotide sequencing reactions.

6. The method according to claim 4, wherein the DNA fragments are produced in nucleic acid amplification reaction.

7. The method according to claim 4, wherein the DNA fragments are fluorecently labeled.

8. The method according to claim 7, wherein the first sample further comprises a first lane indicator, the second sample further comprises a second channel indicator, wherein the first and second channel indicators may be distinguished from one another.

9. The method of claim 8, wherein the indicators are labeled with a fluorescent label that is distinguishable from the fluorescent labels on the DNA fragments.

10. A method of distinguishing between channels of an electrophoresis apparatus, said method comprising loading an electrophoresis apparatus with a plurality of samples by the method of claim 8, further comprising,
    separating the samples in the electrophoresis apparatus,
    detecting the first and second channel indicators, and
    identifying the channel indicators in a plurality of channels of the apparatus.

11. A method according to claim 10 wherein the indicators are labeled with a fluorescent label that is distinguishable from the fluorescent labels on the DNA fragments.

12. A reagent set for loading an analytical instrument having a plurality of sample receiving loading ports, said set comprising,
    a first sample addition reagent comprising,
    a first sample marker and a first channel indicator, and a
    a second sample addition reagent comprising,
    a second sample marker and a second channel indicator, wherein a detectable signal is produced if the first sample marker contacts the second sample marker, and wherein the first indicators can be distinguished from the second indicators.

13. The reagent set according to claim 12, wherein the first indicator can be distinguished from the second indicators on the basis of fluorescent labels.

14. The reagent set according to claim 12, wherein the first indicator can be distinguished from the second indicators on the basis migration rate.

15. The reagent set according to claim 12, wherein the first indicator can be distinguished from the second indicators on the basis migration rate and on the basis of fluorescent labels.

16. The reagent set according to claim 12, wherein the detectable signal produced by the combination of the first sample marker and the second sample marker is a color signal.

* * * * *